(12) United States Patent
Kershman et al.

(10) Patent No.: US 11,654,091 B1
(45) Date of Patent: May 23, 2023

(54) HYDROPHOBIC TOPICAL LOTION FOR SWIMMERS TO REDUCE FRICTION WHEN SWIMMING

(71) Applicant: Shear Kershman Laboratories, Inc, Chesterfield, MO (US)

(72) Inventors: Alvin Kershman, Chesterfield, MO (US); Jeff Shear, Bonita Springs, FL (US)

(73) Assignee: Shear Kershman Laboratories, Inc, Chesterfield, MO (US)

( * ) Notice: Subject to any disclaimer, the term of this patent is extended or adjusted under 35 U.S.C. 154(b) by 250 days.

(21) Appl. No.: 17/202,061

(22) Filed: Mar. 15, 2021

Related U.S. Application Data

(60) Provisional application No. 62/991,262, filed on Mar. 18, 2020.

(51) Int. Cl.
| | |
|---|---|
| *A61K 8/04* | (2006.01) |
| *A61K 8/37* | (2006.01) |
| *A61K 8/34* | (2006.01) |
| *A61K 8/73* | (2006.01) |
| *A61K 8/92* | (2006.01) |
| *A61Q 19/00* | (2006.01) |

(52) U.S. Cl.
CPC ............... *A61K 8/04* (2013.01); *A61K 8/042* (2013.01); *A61K 8/345* (2013.01); *A61K 8/375* (2013.01); *A61K 8/735* (2013.01); *A61K 8/922* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,797,272 | A * | 1/1989 | Linn | A61K 8/064 424/59 |
| 5,500,216 | A * | 3/1996 | Julian | A61Q 17/00 424/78.03 |
| 5,919,398 | A | 7/1999 | Nakamura | |
| 6,287,581 | B1 | 9/2001 | Krzysik | |
| 9,468,600 | B2 | 10/2016 | Danos | |
| 2006/0122282 | A1* | 6/2006 | Leonard | A61K 31/07 514/763 |
| 2010/0233292 | A1* | 9/2010 | Rocker | A61P 31/02 424/642 |
| 2020/0009184 | A1 | 1/2020 | Akthakul | |

OTHER PUBLICATIONS

The Naked Scientists (https://www.thenakedscientists.com/articles/questions/what-would-happen-if-you-covered-swimmer-hydrophobic-substance, Mar. 22, 2016) (Year: 2016).*
Cosmetics & Toiletries, https://www.cosmeticsandtoiletries.com/formulas-products/sun-care/article/21836290/very-water-resistant-sunscreens, Mar. 20, 2014 (Year: 2014).*

* cited by examiner

*Primary Examiner* — Craig D Ricci
(74) *Attorney, Agent, or Firm* — Linda L. Lewis

(57) ABSTRACT

A lotion for the topical application to reduce a swimmer's friction when swimming in water made by combining an aqueous phase comprising and at least one humectant with an oil phase. The at least one humectant is present in the aqueous phase in the range of from 45 to 97 wt. %. The oil phase comprises at least one surfactant and at least one oil, and is present in the lotion in the range of about 5 to 45 wt. %. The surfactant is present in the oil phase in the range of from about 0.1 to 25 wt. %. The lotion is stable, homogenous and hydrophobic, and reduces friction when swimming in water, with the lotion applied to a swimmer.

8 Claims, No Drawings

HYDROPHOBIC TOPICAL LOTION FOR SWIMMERS TO REDUCE FRICTION WHEN SWIMMING

CROSS-REFERENCE TO RELATED APPLICATIONS

This application claims the benefit of provisional patent application No. 62/991,262 filed Mar. 18, 2020, which is hereby incorporated by reference.

STATEMENT REGARDING FEDERALLY SPONSORED RESEARCH

Not Applicable.

APPENDIX

Not Applicable.

TECHNICAL FIELD

The present invention relates to a hydrophobic topical lotion for swimmers to reduce friction when swimming in water.

BACKGROUND OF THE INVENTION

Individuals who participate in water sports such as competition swimmers and water polo players apply materials such as mineral oil, wintergreen oil, petrolatum, etc. to certain body surfaces in order to reduce drag. This reduces friction of the body of the swimmer as she moves through the water and increases swimming speed. The oily or greasy substances that are in use can damage pool filters and motors and are not readily removed from pool water by filtration. They must be applied to dry skin, and are applied as a thick coat or film since these materials tend to wash off by the action of the water current as one swims through the water. The film closes skin pores interfering with sweating and respiration of the skin. Additionally, the oily or greasy materials can spill or drip during application causing a hazardous condition in the locker room or on the deck surfaces adjacent to a swimming pool.

U.S. Pat. No. 5,500,216 discloses a hydrophobic, topical lotion to reduce swimmer drag comprising a uniform suspension of a long acting composition formed by a mixture of 2 hydrophobic metal oxides in vaporizable liquid carrier such as ethanol containing a vaporizable plasticizer such as propylene glycol in which the amount of the larger hydrophobic metal oxide particles in the mixture predominates over the amount of smaller particles of hydrophobic metal oxide. This product has limited effectiveness.

Topical creams or ointments are disclosed in U.S. Pat. No. 5,919,398. U.S. Pat. No. 9,468,600 discloses a transdermal composition. Some of these patents disclose the use of hydrophobic silica compounds, which are not used or claimed in the present invention.

The present invention is a hydrophobic tropical lotion for swimmers that reduces friction when swimming in water and can be applied to wet skin as well as dry skin to effectively adhere and reduce friction.

SUMMARY OF THE INVENTION

The present invention is a homogeneous hydrophobic topical lotion for swimmers wherein the lotion contains form about 0.1 to 25 wt. % surfactant, from about 0.25 to 35 wt. % oil, from about 45 to 97 wt. % humectant, optionally from about 0.01 to 5.0 wt. % gelling agent, and from about 1 to 40 wt. % water.

The present invention is made by combining an aqueous phase comprising at least one humectant with an oil phase to form a topical lotion with hydrophobic properties. The at least one humectant is present in the aqueous phase in the range of from about 45 to about 99 wt. %. The oil phase comprises at least one surfactant and at least one oil. The surfactant is present in the oil phase in the range of from about 3 to 99 wt. %. The aqueous phase is added to the oil phase in a weight ratio of about 20:1 to 1:2. The aqueous phase is added to the oil phase using low to medium shear mixing to provide the homogeneous hydrophobic topical lotion. The hydrophobic lotion can be applied to wet skin or dry skin and adheres to the skin and provides reduced friction properties to the skin when immersed in water.

The present invention is also a method of reducing friction on a swimmer when swimming through water by applying to wet or dry skin an effective amount of the above-described homogeneous hydrophobic topical lotion.

It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

The oil phase is prepared from a hydrophobic solution or mixture containing optionally at least one oil or petroleum distillate and at least one surfactant. The surfactant is preferably a non-water soluble surfactant having an HLB number of less than about 6, and includes emulsifiers. Examples of suitable surfactants include oleic acid, acetylated monoglycerides, glycerol dioleate, sorbitan tristearate, glycerol monoleate, and various combinations of these. A preferred surfactant is commercially sold as ATMOS® 300K, and is a combination of mono- and di-glycerides made from edible food sources and propylene glycol with an HLB of about less than 4.0. In a preferred embodiment, the surfactant has an HLB of about 2.8.

In a preferred embodiment, the oil phase contains a second surfactant that has an HLB number of about 6. The preferred surfactant is glyceryl monostearate and has an HLB of about 5.8. In a more preferred embodiment, the ratio of ATMOS®300K surfactant to the glyceryl monostearate is about 10:1. The surfactant is present in the oil phase in the amount of about 3 to 99 wt. %, and the oil is present from about 97 to 1.0 wt. %. The oil suitable for the oil phase is typically liquid or semi-solid at room temperature, and is compatible with the topical applications. Such oils include essential oils, plant oils, such as vegetable oil, corn oil, canola oil, coconut oil, castor oil or olive oil, shea butter, and animal fats such as tallow and lard. The oils include petroleum distillates, such as petrolatum and mineral oil. Mixtures of oils are also contemplated in the present invention. The oil phase is present in the lotion in the range of from about 5 to 45 wt. %. In a preferred embodiment, the surfactant and the oil are present in the lotion in a weight ratio of about 5:1 to 1:4 surfactant to oil.

The aqueous phase contains at least one humectant. Suitable humectants include, but are not limited to glycerin, lactic acid, polyols, propylene glycol, corn syrup, high fructose corn syrup (HFCS), including Cornsweet 55 (55 wt. % fructose, 24 wt. % water and 21 wt. % glucose) and Cornsweet 42 (42 wt. % fructose, 24. wt. % water and 34 wt. % glucose), and sorbitol. The preferred form of humectant is non-crystallizing liquid sorbitol (70 wt. % sorbitol in water). The at least one humectant is present in the aqueous phase from 45 to 97 wt. %. Preferably, the amount of humectant in the lotion is from about 60 to 97 wt. %. More preferably, the amount of humectant in the lotion is from about 70 to 95 wt. %.

A preferred combination of humectants is glycerol, sorbitol solution and high fructose corn syrup. More preferably the humectants in the lotion are from about 10 to 60 wt. % glycerol, from about 5 to 50 wt. % sorbitol solution, and from about 0 to 20 wt. % high fructose corn syrup. A preferred high fructose corn syrup is Cornsweet 55 and preferred sorbitol solution is non-crystalizing liquid sorbitol 70 wt. %.

Various gelling agents can be employed including, for example and without limitation, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, the carbomers and carbopols, polyvinylpyrrolidone, polyethylene glycol, polyethylene oxide, polyvinyl alcohol, other polymeric materials, and mixtures thereof, etc. The pectin or pectic substances useful for this invention include not only purified or isolated pectates but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange. Preferred gelling agents are hyaluronic acid or its salt, carboxymethyl cellulose (CMC), guar gum, and a combination of guar gum and xanthan gum in the range of about 0.01 to 2.0 wt. %.

The claimed composition is typically prepared using a planetary or counter rotating type mixer having a rubber lined mixing bowl equipped with a wire whip stirring device. Preferably, the wire whip is rubber coated. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the lotion is conducted as follows:

Aqueous Phase:
1. In suitable container with lid, measure accurately, the Water and Hyaluronic Acid. Shake well and refrigerate. Store overnight.
2. The next day, into a beaker of suitable size, accurately weigh the aqueous phase ingredients with the mixture from Step 1, and mix well.

Oil Phase:
1. Accurately weigh all oil phase into the kitchen aid bowl.
2. Warm ingredients until homogeneously melted (10° F. above the highest melt point ingredient).

Mixing:
1. Keep the kitchen aid mixing on low speed and relatively low shear (30-600 rpm's) with the oil phase ingredients melted.
2. Drop by drop, begin adding the Aqueous Phase ingredients to the bowl while continuing to mix at low speed.
3. As lotion starts to form, aqueous phase solution is added faster until a slow pour or is achieved. When 50% of the aqueous phase solution is added, mixer speed should be increased to no more than setting 3 on the kitchen aid. (Stir speed (rpm) can vary from one mixer to the next, so the correct setting must be determined for each mixer).
4. Continue adding until all of the aqueous phase solution is in, taking care to scrape the beaker out, making sure all of the solution is removed.
5. Stop the mixer and scrap down the bowl and mixing blade.
6. Continuing mixing at speed 3 or 4 for an additional ten (10) minutes to produce the hydrophobic lotion.

The components of the hydrophobic lotion have the following preferred wt. % ranges:

Oil Phase:
Surfactant: 0.1-25.0
Oil: 0.25-35.0
Aqueous Phase:
Water: 1.0-40.0
Gelling agent: 0.01-5.0

In a preferred embodiment, the wt. % ranges for specific components are:
ATMOS®300 1.0-20.0
Citation 70 0.5-15.0
Coconut Oil 0.25-10.0
Glyceryl Stearate 0.1-5.0
Shea Butter 0.25-10.0
Sorbitol Solution 5.0-50.0
Glycerin 10.0-60.0
HF Corn Syrup 1.0-20.0
Hyaluronic Acid 0.01-2.0
Water 1.0-40.0

In a second embodiment of the process of this invention, the lotion is prepared as a first step and a second step. The first step produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 20:1 to 1:2), this initial process step is concluded.

The second step begins with the seed batch of the first step, at the desired final weight ratio of aqueous phase to oil phase. The volume of seed material needed for the second step is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

An embodiment is shown in Examples 1-4, below.

TABLE 1 Method of Preparing the Hydrophobic Topical Lotion

Example 1

| Hydrophobic Topical Lotion | | |
|---|---|---|
| Ingredient | Weight | % |
| Oil Phase | | |
| ATMOS ® 300K - surfactant | 15.0 | 5.00 |
| Citation 70 - mineral oil | 12.0 | 4.00 |
| Coconut Oil, Organic Extra Virgin | 6.0 | 2.00 |
| Glyceryl Monostearate (GMS) emulsifier | 1.5 | 0.50 |
| 100% Raw Shea Butter - lipid | 3.0 | 1.00 |
| Aqueous Phase | | |
| Sorbitol Solution 70% USP - humectant | 75.0 (22.5 water, 52.5 sorbitol) | 25.00 (7.5 water, 17.5 sorbitol) |
| Glycerin, USP 99.7% Excipient/Food use - humectant | 150.0 | 50.00 |
| Cornsweet 55 HFC - humectant | 15.0 (3.6 water, 11.4 sugars) | 5.00 (1.2 water, 3.8 sugars) |
| Hyaluronic Acid Pure Powder-gelling agent | 0.225 | 0.075 |
| purified water (Distilled) | 22.275 | 7.425 |
| Total | 300.00 | 100.0 |

A. Preparing the Aqueous Phase (88.0 wt. % of the final lotion)

1. In suitable container with lid, measure carefully and accurately, the water and Hyaluronic Acid. Shake well and refrigerate. Store overnight.

2. Mix the sorbitol solution, glycerin and Cornsweet 55 together. Mix well and warm to 43.33° C.

3. Remove heat source.

A. Preparing Oil Phase (12.0 wt. % of final lotion)

1. Warm citation 70 (mineral oil), Coconut Oil, and Shea Butter to 26.7° C.

2. Add ATMOS® 300K and Glyceryl Monostearate, mix well and set aside.

C. Forming the lotion

1. Using a 5 quart lab Hobart type planetary lab/kitchen mixer with a rubber or plastic lined wire whip and rubber or plastic lined bowl add 40 g of oil phase and stir on #2 setting.

2. Slowly add approx. 200-300 g aqueous phase with mixing.

3. Add remainder of the oil phase to the bowl. Slowly add remainder of the aqueous phase to the bowl with mixing. Scrape the sides of the bowl with a spatula to ensure thorough mixing.

4. Increase the speed to #4 for 10 minutes more, making sure to scrape the sides of the bowl occasionally. After 10 minutes, the lotion is prepared.

The lotion of Example 1, Table 1, above, is a homogeneous hydrophobic lotion that adheres to wet or dry skin, and reduces friction for swimmers.

The lotion of Examples 1-4, were prepared as above and were tested as follows:

Stability Test 1

A small amount of lotion is placed on a clear glass plate or slide. Using another glass plate, the lotion is spread to a thin layer having a continuous oil film on its surface. The lotion is visually observed at 1 hour, 4 hours and 24 hours from preparation. Any evidence of cracking of the continuous film or leaking of the aqueous phase from the lotion onto the plate is an indication of product fail.

Stability Test 2

Deionized water is placed in a small beaker and about 10 g of lotion is added to the water. The lotion in water is visually observed at 1 hour, 4 hours and 24 hours from adding to water. The lotion should expand (increase in size) as the lotion absorbs water. The lotion fails if it dissolves completely in the water or breaks into pieces which further break apart when moved with spoonula. It also fails if the aqueous phase leaks out into the water.

Example 2

| Ingredient | Weight | % |
|---|---|---|
| Oil Phase | | |
| ATMOS ® 300K | 18.0 | 6.00 |
| Citation 70 mineral oil | 12.0 | 4.00 |
| Vitamin E 1300IU (Natural Source) | 1.5 | 0.50 |
| Glyceryl Stearate (GMS) | 6.0 | 2.00 |
| Coconut Oil, Organic Extra Virgin | 3.0 | 1.00 |
| 100% Raw Shea Butter | 4.5 | 1.50 |
| Aqueous Phase | | |
| Sorbitol Solution 70% USP | 120.0 | 40.00 |
| Glycerin, USP 99.7% Excipient/Food use | 120.0 | 40.00 |
| Cornsweet 55 HFC | 15.0 | 5.00 |

Example 3

| Ingredient | Weight | % |
|---|---|---|
| Oil Phase | | |
| ATMOS ®300K | 13.8 | 4.60% |
| Citation 70 mineral oil | 19.2 | 6.40% |
| Glyceryl Stearate (GMS) | 4.5 | 1.50% |
| Coconut Oil, Organic Extra Virgin | 7.5 | 2.50% |
| Aqueous Phase | | |
| Sorbitol Solution 70% USP | 90.0 | 30.00% |
| Glycerin, USP 99.7% Excipient/Food use | 150.0 | 50.00% |
| Cornsweet 55 HFC | 15.0 | 5.00% |

Example 4

| Ingredient | Weight | % |
|---|---|---|
| Oil Phase | | |
| ATMOS ® 300K | 19.5 | 6.50% |
| Citation 70 mineral oil | 12.0 | 4.00% |
| Vitamin E 1300IU (Natural Source) | 1.5 | 0.50% |
| Glyceryl Stearate (GMS) | 7.5 | 2.50% |
| Coconut Oil, Organic Extra Virgin | 4.5 | 1.50% |

-continued

| Ingredient | Weight | % |
| --- | --- | --- |
| Aqueous Phase | | |
| Sorbitol Solution 70% USP | 112.5 | 37.50% |
| Glycerin, USP 99.7% Excipient/Food use | 112.5 | 37.50% |
| Cornsweet 55 HFC | 15.0 | 5.00% |
| Hyaluronic Acid Pure Powder | 0.15 | 0.05% |
| purified water (Distilled) | 14.85 | 4.95% |

A method of using the lotion of Examples 1-4 comprises a swimmer applying about an ounce of lotion to the palm of her hand, rubbing her hands together, and applying the lotion to her skin by gently pressing it into her skin with slow sweeping motions until all desired areas (shoulders, arms, back, face, and legs) are covered with a thin layer. The lotion is rubbed into the skin until it feels smooth and soft.

The application of the homogeneous, hydrophobic topical lotion to the swimmer's skin had resulted in an increase in the swimmer's swim speed of as much as 10% due to decreased water friction.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of reducing a swimmer's friction when swimming in water comprising topically applying to the skin of a swimmer in need thereof a lotion comprising:
   from about 45 to 97 wt. % at least one humectant;
   from about 0.01 to 5.00 wt. % gelling agent;
   from about 1.0 to 40.0 wt. % water;
   from about 0.25 to 35 wt. % at least one oil;
   from about 0.1 to 25 wt. % at least one surfactant; and
   wherein the lotion is stable, homogeneous and hydrophobic; and
   wherein when topically applied adheres to wet and dry skin.

2. The method of claim 1, wherein the surfactant is selected from the group consisting of oleic acid, acetylated monoglycerides, glycerol dioleate, sorbitan tristearate, glycerol monoleate, glyceryl monostearate, propylene glycol monoglyceride, propylene glycol diglyceride and combinations thereof.

3. The method of claim 2, wherein the humectant is present in the lotion from about 60 wt % to about 97 wt %.

4. The method of claim 3, wherein the humectant is selected from the group consisting of glycerine, lactic acid, polyols, propylene glycol, high fructose corn syrup, and sorbitol.

5. The method of claim 4, wherein the wherein the gelling agent is selected from the group consisting of hyaluronic acid, the salt of hyaluronic acid, carboxymethyl cellulose, guar gum, and a combination of guar gum and xanthan gum.

6. The method of claim 4, wherein the gelling agent is present from about 0.01 to 2.0 wt. %.

7. The method of claim 5, wherein the swimmer's friction is reduced when swimming in water.

8. The method of claim 5, wherein the lotion is prepared by the method comprising:
   mixing the water and the hyaluronic acid and refrigerating overnight to prepare a gelling agent mixture;
   mixing the gelling agent mixture with the at least one humectant to prepare an aqueous phase;
   heating to melt and mixing together the at least one oil and the at least one surfactant and placing in a mixing bowl to prepare an oil phase;
   mixing the oil phase in the mixing bowl using a mixer set on low shear speed and adding the aqueous phase to the mixing bowl, drop by drop to form a lotion;
   adding the aqueous phase faster until a slow pour or is achieved;
   increasing the mixing speed to the low-medium shear mixing speed when about 50% of the aqueous phase solution has been added and adding remainder of the aqueous phase; and
   continuing mixing for an additional about ten minutes to produce the homogeneous hydrophobic lotion.

* * * * *